United States Patent [19]
Gubarev et al.

[11] Patent Number: 6,149,912
[45] Date of Patent: Nov. 21, 2000

[54] METHOD TO ENHANCE INNATE IMMUNITY DEFENSE MECHANISMS BY TREATMENT WITH PLANT-DERIVED ALKALOIDS

[76] Inventors: Michael J. Gubarev; Elena Y. Enioutina, both of 1658 E. Westminister Ave., Salt Lake City, Utah 84105

[21] Appl. No.: 09/130,316

[22] Filed: Aug. 7, 1998

Related U.S. Application Data

[63] Continuation of application No. 08/879,970, Jun. 20, 1997, abandoned.

[51] Int. Cl.$^7$ ...................................................... A61K 35/78
[52] U.S. Cl. ........................................... 424/195.1; 514/26
[58] Field of Search ............................ 424/195.1; 514/26

[56] References Cited

U.S. PATENT DOCUMENTS 5,681,950   10/1997   Echeverri-Lopez et al. .............. 540/80

OTHER PUBLICATIONS

Bomford et al., Vaccine 10(9): 572–577 (1992).
Wu, R.T. et al., J. of Ocular Pharmacology, vol. 6(4), p. 301–311, 1990.
Bahr, V. et al., J. of Medicinal Plant Research, vol. 44(1), p. 32–33, Jan. 1982.
Nadeem, M. et al., Hamdard Medicus, vol. 39(4), p. 25–27, 1996.
Wu, R.T. et al., Int. J. Immunopharmacology, vol. 12(7), p. 777–786, 1990.
Budhiraja, R.D. et al., J. of Scientific & Industrial Research, vol. 46(11), p. 488–491, Nov. 1987.
Costa, Scott D. et al., "Sensitivity of Beauveria bassiana to Solanine and Tomatine . . . " Journal of Chemical Ecology, vol. 15, No. 2, pp. 697–706, 1989.
Fewell, Alison M. et al., "Interactions Between The Glycoalkaloids Solasonine . . . " Phytochemistry, vol. 37, No. 4, pp. 1007–1011, 1994.
Keukens, Erik A.J. et al., "Molecular basis of glycoalkaloid induced membrane disruption" Biochimica et Biophysica Acta, pp. 216–228, 1995.
Slanina P., "Solanine (Glycoalkaloids) In Potatoes: Toxicological Evaluation" Chem. Toxic, vol. 28, No. 11, pp. 759–761, 1990.
Phillips, B. J. et al., "A study of the Toxic Hazard . . . " Food and Chemical Toxicology 34 pp. 439–448, 1996.
Thorne, H.V. et al., "The inactivation of Herpes Simplex Virus . . . " Antiviral Research, 5 pp. 335–343, 1985.

*Primary Examiner*—Jean C. Witz

[57] ABSTRACT

The present invention relates to a method for enhancing innate immunity defense mechanisms of vertebrate animals including humans. In accordance with the present invention, innate immunity defenses are enhanced by the administration of plant-derived immunomodulators. These plant-derived immunomodulators may be plant tissues, plant extracts containing steroid-like glycoalkaloids, or plant-derived glycoalkaloids. The administration of these immunomodulators significant augments the antimicrobial activities of the innate immune system. The glycoalkaloids useful for the present invention have the formula R—$R^1$, wherein R is a mono-, di-, tri- or oligo-saccharide which may optionally be modified with pharmacologically acceptable esters or ethers and $R^1$ is an aglycon or derivative as defined herein. Preferred plant-derived glycoalkaloids include solanine and chaconine.

18 Claims, 3 Drawing Sheets

METHOD TO ENHANCE INNATE IMMUNITY DEFENSE MECHANISMS BY TREATMENT WITH PLANT-DERIVED ALKALOIDS

This application is a continuation of U.S. patent application Ser. No. 08/879,970, filed Jun. 20, 1997 now abandoned, which is incorporated herein by reference in its entirety.

BACKGROUND OF THE INVENTION

The present invention relates to a method for enhancing innate immunity defense mechanisms of vertebrate animals including humans. In accordance with the present invention, innate immunity defenses are enhanced by the administration of plant-derived immunomodulators. These plant-derived immunomodulators may be plant extracts containing steroid-like glycoalkaloids or plant-derived glycoalkaloids. The administration of these immunomodulators significantly augments the antimicrobial activities of the innate immune system. Preferred plant-derived glycoalkaloids include solanine and chaconine.

The publications and other materials used herein to illuminate the background of the invention and in particular cases, to provide additional details respecting the practice, are incorporated by reference, and for convenience are numerically referenced in the following text and respectively grouped in the appended bibliography.

Over the past 50 years, chemical antibiotics have provided clinicians with effective therapies for the prevention, treatment, cure, plus the elimination of horizontal or vertical transmission, of many species of microorganisms capable of causing disease. These successes, however, have led to a high degree of complacency concerning the inevitable threat of acquired bacterial drug resistance. Over the past decade alone, both the frequency and spectrum of multiresistant species of pathogenic bacteria has dramatically increased (1–4). Unfortunately, few new antimicrobial drugs are reported to be under active development (3, 4). Assuming this trend continues, a major clinical problem that we will certainly face early in the 21st century, will be increased numbers of untreatable bacterial infections. Even today, there are species of Streptococcus, Staphylococcus, Pseudomonas, Enterococcus, and Mycobacterium which have developed resistance to all currently available antibiotic therapies (5–8).

It is highly unlikely that specific vaccines for the many pathogenic microorganisms capable of causing disease can be developed rapidly enough to replace our present dependence on antibiotics. In spite of their exceptional effectiveness in the prophylactic treatment against diseases like tetanus, diphtheria, whooping cough, polio, and smallpox, the number of available vaccines is extremely small in comparison to the vast array of different species and strains of bacteria that can cause infectious diseases. Consequently, new strategies need to be pursued to meet the upcoming challenges that are being caused by the emergence of multidrug resistance in bacteria.

Host protection against diseases caused by infectious agents is provided by the immune system, a collection of molecular and cellular mechanisms and processes which function synergistically to either rid the host of the offending agents or control their proliferation (9–16). The innate defense mechanisms of the immune system get involved early postinfection, and their function is to control the extent of infection in an agent nonspecific manner. The generation of acquired or adaptive immunity, with its antigen specificity and high degree of efficiency takes a period of time to develop. Individuals can vary greatly in the efficiency of their innate immune defenses. These differences can spell the difference between an infection which resolves prior to development of overt disease, and an infection which progresses to full-blown disease prior to the mobilization of the acquired immune defense mechanism.

Herbal drugs are broadly represented in the Pharmacopeiae of many countries, including the USA. (23). Currently, 50 drugs discovered from plants are produced by domestic pharmaceutical companies (24). These phytomedicinals play important roles in treating disorders of the digestive, respiratory, cardiovascular, nervous, endocrine, and other organ systems (24, 25). The immune system is also responsive to the therapeutic influences of plant derived compounds. Among these are triterpeniod saponin glycosides from Ginseng, sterols from Eleuthero, high molecular weight polysaccharides (heteroxylan, arabinogalactan) and low molecular weight derivatives (chicoric acid) from Echinacea (25). These substances have no direct bactericidal or bacteriostatic properties (25, 26); rather, their beneficial effects on the immune system are brought about by their ability to increase innate immune defense mechanisms, and in particular, stimulation of phagocytosis, promotion of lymphocyte activity, and increased cytokine (TNF-alpha; IFN-gamma) production (25–27). These responses allow the neutralization of some viruses and destruction of bacteria (27, 28).

Modern Chinese medicine utilizes the antimicrobial and antiviral properties of some plants. A polysaccharide complex, lentinan (a derivative of the Shiitake mushroom (Lentinus edodes), came into current clinical use from traditional ancient medicine because of its ability to strengthen the immune system (29).

Sprouts and foliage of Solanum species, including potatoes (Solanum tuberosum L.), and tomatoes (Lycopersicum esculentum), are sources of steroid-like glycoalkaloids which contain a steroid-like aglycon bound to an oligosaccharide moiety (20). There are numerous publications concerning the toxicology of glycoalkaloids in potatoes and tomatoes (18, 19, 30–37). At high concentrations, the major glycoalkaloids of potatoes (solanine and chaconine) and some minor ones can cause poisoning (18, 34, 36). Factors such as environmental or geographic variations, exposure to light (green potatoes), or mechanical damage (harvesting) may result in a critical elevation of glycoalkaloid concentrations in tubers (38, 39). Toxic doses of glycoalkaloids (over 5 mg/kg/body weight) might have disruptive effects on membranes in the gastrointestinal tract and elsewhere. These effects are presumably due to saponine-like properties and can lead to hemolytic and hemorrhagic damage of organs (40). Taken in high doses, glycoalkaloids also inhibit acetylcholinesterase (41) and increase the activity of ornithine decarboxylate (42), which can cause liver dysfunction. Since green potatoes, sprouts, and potato plants contain potentially dangerous levels of glycoalkaloids, they are not recommended for consumption. However, recent studies conducted among some Bangladeshi communities, which consume potato tops (leaves) as regular food, revealed that moderate quantities of glycoalkaloids (below 4 mg/kg/body weight/day) are unlikely to represent a health hazard to humans (12). There are a few reports indicating that some glycoalkaloids from the Solanaceae family at moderate concentrations show direct antiviral and antifungal activities (43–46). No bactericidal or bacteriostatic effect has been described for potato alkaloids, including aglycons, and for triterpenoid compounds from ginseng (25), which have structural similarities to steroid-like aglycons (47).

It is desired to identify compounds which will enhance innate immune defense mechanisms to aid in the battle against infections and which will prove useful in treating antibiotic resistant microbes.

SUMMARY OF THE INVENTION

The present invention relates to a method for enhancing innate immunity defense mechanisms of vertebrate animals including humans. In accordance with the present invention, innate immunity defenses are enhanced by the administration of plant-derived immunomodulators. These plant-derived immunomodulators may be plant extracts containing steroid-like glycoalkaloids or plant-derived glycoalkaloids. The administration of these immunomodulators significantly augments the antimicrobial activities of the innate immune system. The glycoalkaloids useful for the present invention have the formula R—$R^1$, wherein R is a mono-, di-, tri- or oligo-saccharide moiety as defined below and $R^1$ is an aglycon or derivative as defined below. Preferred plant-derived glycoalkaloids include solanine and chaconine.

DETAILED DESCRIPTION OF THE INVENTION

Figure 1A:
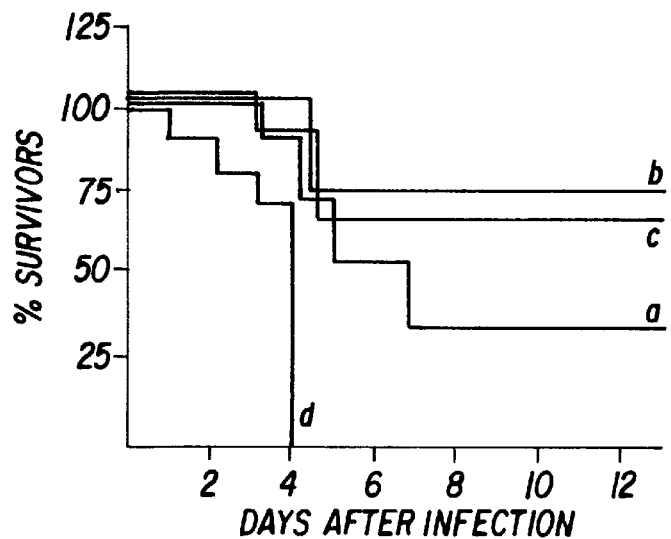
FIG. 1A. Lifespan monitoring of normal adult mice pretreated with solanine and challenged intraperitoneally with 25 $LD_{50}$ of Salmonella typhimurium (S. typhimurium). Each group of 10 mice was given solanine i.p. 14 days before challenge at the indicated doses: (a) 0.1 μg per mouse; (b) 1.0 μg per mouse; (c) 10.0 μg per mouse; (d) naive controls received only saline.

The most important function of the immune system is to provide its host with protection against disease. To carry out these tasks, a large and diverse array of effector mechanisms have evolved, the majority of which exhibit antigen specificity. Each individual effector mechanism possesses a degree of uniqueness with respect to its ability to influence the rate of progression, to detoxify, or to promote the elimination of microbial pathogens. Such a diversity in available mechanisms is absolutely essential since no single effector response can effectively deal with all forms of pathogenic insults.

The different mechanisms employed to protect a host against microbes include physical barriers, phagocytic cells in the blood and tissues, natural killer cells and various blood-borne molecules. These mechanisms can repel, destroy or hold in check many classes of microbes. Some of these defense mechanisms (a) are present prior to exposure to infectious microbes or foreign macromolecules, (b) do not discriminate among most foreign substances, and (c) frequently cannot be sufficiently enhanced by such exposure. These defense mechanisms are the components of the innate immunity. Other defense mechanisms are induced or stimulated by exposure to foreign substances, are specific for distinct macromolecules and increase in magnitude and defensive capabilities with each successive exposure to a particular macromolecule. These mechanism constitute adaptive (acquired) immunity.

The innate defense mechanisms of the immune system get involved early postinfection, and their function is to control the extent of infection in an agent nonspecific manner. Individuals can vary greatly in the efficiency of their innate immune defenses. These differences can spell the difference between an infection which resolves prior to development of overt disease, and an infection which progresses to full-blown disease prior to the mobilization of the acquired immune defense mechanisms. In addition, the frequency and spectrum of multiresistant species of pathogenic bacteria has dramatically increased over the past decade. Consequently, new strategies need to be pursued to meet the upcoming challenges that are being caused by the emergence of multidrug resistance in bacteria and to assist individuals having an innate immune response which is not operating optimally. One strategy to achieve these goals is to enhance the innate immune response in individuals.

The present invention relates to a method for enhancing innate immunity defense mechanisms of vertebrate animals including humans. In accordance with the present invention, innate immunity defenses are enhanced by the administration of plant-derived immunomodulators. These plant-derived immunomodulators may be plant extracts containing steroid-like glycoalkaloids or plant-derived glycoalkaloids. The administration of these immunomodulators significantly augments the antimicrobial activities of the innate immune system. Preferred plant-derived glycoalkaloids include solanine and chaconine.

As used herein, the term "immunomodulator" refers to an agent which is able to modulate an immune response. In the context of the present invention, such modulation is an enhancement of an innate immunity defense mechanism.

As used herein, the term "individual" refers to a vertebrate, and includes, but is not limited to domestic animals, sports animals and primates, including humans.

As used herein, the term "infectious agent" refers to bacteria, fungi and protozoa.

The term "effective amount" of an immunomodulator refers to an amount of an immunomodulator sufficient to enhance a host defense mechanism, as more fully described below. This amount may vary to some degree depending on the mode of administration, but will be in the same general range. If more than one immunomodulator is used, each one may be present in these amounts or the total amount may fall within this range. The exact effective amount necessary could vary from subject to subject, depending on the species, age and general condition of the subject, the severity of the condition being treated, the mode of administration, etc. Thus, it is not possible to specify an exact effective amount. However, the appropriate effective amount may be determined by one of ordinary skill in the art using only routine experimentation or prior knowledge in the immunomodulator art.

In accordance with the present invention, protection against diseases caused by infectious agents is provided by the enhancement of the host's innate immune system through treatment with plant-derived immunomodulators. The administration of plant extracts (e.g., a water-alcohol extract) containing steroid-like glycoalkaloids, such as solanine or chaconine, significantly augments the antimicrobial activities of the innate immune system. The glycoalkaloid containing extracts are prepared from Solanum species, Veratrum species and Liliaceae species. As shown in detail below, mice prophylactically treated with low doses of Solanum extract containing solanine plus chaconine, or with individual glycoalkaloids, were rendered resistant to challenge with lethal doses of *Salmonella typhimurium.* Single or multiple treatment(s) with these glycoalkaloid compounds, but not with the aglycon, provided mice with significant protection against infection. Treated animals were able to rapidly clear bacteria from their target organs. Similar results are shown for mice against infection by *Francisella tularensis, Pseudomonas aeruginosa,* or *Candida albicans.* Thus, the innate immunity enhancing effect is not antigen specific. The wide applicability of this effect is demonstrated by the protection afforded baby pigs from lethal doses of *Salmonella choleraesius.* The enhancement of innate defenses offers an alternative to antigen-specific vaccines or prophylactic antibiotic treatment, both of which may be limited by resistant organisms or lack of specificity due to bacterial genomic diversity.

The innate immune defense mechanisms are enhanced by administrating an effective amount of the plant-derived immunomodulator, e.g., a plant, a plant extract containing glycoalkaloids or purified plant glycoalkaloids. The plant extract preferably contains 0.1 to 10%, more preferably, 1 to 5%, and most preferably 1% glycoalkaloids. The glycoalkaloids useful for the preset invention have the formula R—$R^1$. In accordance with the present invention, R is a mono-, di-, tri-, or oligo-saccharide which may optionally be modified with pharmacologically acceptable esters or pharmacologically acceptable ethers. $R^1$ is an aglycon or derivative having the general formulas:

I 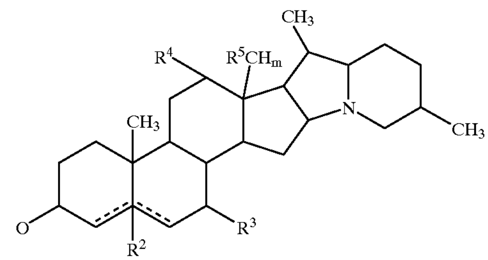 or

II 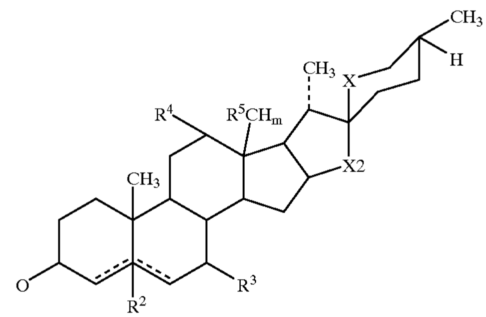 wherein $R^2$ is H when neither of the dashed lines is a double bond or is nothing when one of the dashed lines is a double bond;

$R^3$, $R^4$ and $R^5$ are independently H, OH, =O, pharmacologically acceptable esters or pharmacologically acceptable ethers;

X and X2 are independently N or O; and m is 1 or 2.

Examples of $R^1$ include solanidine ($R^2$ is nothing with a 5–6 double bond, $R^3$, $R^4$ and $R^5$ are H and m is 2 in formula I), rubijervine ($R^2$ is nothing with a 5–6 double bond, $R^3$ and $R^5$ are H, $R^4$ is OH and m is 2 in formula I) and isorubijervine ($R^2$ is nothing with a 5–6 double bond, $R^3$ and $R^4$ are H, $R^5$ is OH and m is 2 in formula I). Preferred plant glycoalkaloids are solanine ($R^1$ is solanidine and R is the trisaccharide glucose-galactose-rhamnose) or chaconine ($R^1$ is solanidine and R is the trisaccharide rhamnose-glucose-rhamnose) or a mixture thereof.

The plant-derived immunomodulator is preferably administered parenterally or orally in a single unit dose or in a multiple subunit dose. The plant derived immunomodulator is administered once 1–7 days prior to infection (challenge) preferably 5 days before infection, or multiple times 7–14 days prior to infection, preferably by administrations given three times every other day. The prophylactic effect, i.e., an enhanced innate immune response, lasts at least one week following a single treatment, and at least 14 days following multiple (triple) administration of plant-derived immunomodulator. The plant-derived immunomodulator can also be administered in early hours postinfection (24 hours), preferably 1–4 hours postinfection.

Pharmaceutical compositions containing a compound of the present invention as the active ingredient can be prepared according to conventional pharmaceutical compounding techniques. See, for example, *Remington's Pharmaceutical Sciences,* 17th Ed. (1985, Mack Publishing Co., Easton, Pa.). Typically, the active ingredient will be admixed with a pharmaceutically acceptable carrier. The carrier may take a wide variety of forms depending on the form of preparation desired for administration, e.g., parenteral (intravenous, administration by inhalation, rectal, vaginal) or oral (feed/dietary supplement). The compositions may further contain antioxidizing agents, stabilizing agents, dispersing agents, preservatives and the like.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like.

Plants, plant tissues or plant extracts containing steroid-like glycoalkaloids or the plant-derived glycoalkaloids individually or in admixture are administered to a vertebrate animal in an amount sufficient to enhance the innate immune response, especially the anti-infectious agent activities of innate immunity. Typically, the plant extracts containing steroid-like glycoalkaloids exhibit their innate immune enhancing effect at a dosage range from 1.7 mg/kg to 33.5 mg/kg. A preferable dose for extracts administration is 5.0 to 15.0 mg/kg, and a more preferably dose is 6.5 to 10 mg/kg. Usually the plant extracts containing steroid-like glycoalkaloids contain about 1% of the total glycoalkaloid fraction. Thus, concentration of active ingredients administered to animals with the extracts is ten- to a hundred-fold lower than the concentration which might cause poisoning in some individuals (5 mg/kg of pre glycoalkaloids), or than the $LD_{50}$ dose in mice which is 40–50 mg/kg for Solanine/Chaconine (20). The plant-derived glycoalkaloids individually or in admixture of the present invention exhibit their effect at a dosage range of 0.01 mg/kg to 3.0 mg/kg. A preferable dose of the purified plant glycoalkaloids is 0.03 to 1.0 mg/kg, and a more preferred dose is 0.03 to 0.3 mg/kg. A suitable dose can be administered in a single dose or it can be administered in multiple sub-doses per day. Typically, a dose or sub-dose may contain from about 0.1 µg (0.0033 mg/kg) to about 30 µg (1.0 mg/kg) of the active ingredient per unit dosage form. A more preferred dosage will contain from about 0.1 µg (0.0033 mg/kg) to about 10 µg (0.33 mg/kg) of active ingredient per unit dosage form.

The present invention is described by reference to the following Examples, which are offered by way of illustration and are not intended to limit the invention in any manner. Standard techniques well known in the art or the techniques specifically described below were utilized.

EXAMPLE 1

Materials and Methods

Mice: Male CF-1 strain mice were purchased from Sasco Inc. (Wilmington, Mass.) and housed in the University of Utah Animal Facility. Within each experiment, groups of five to ten age-, strain-, and sex-matched mice were used. The age of the mice ranged between 6 and 14 weeks at the onset of the experimental protocols. The University of Utah Animal Resources Center is in compliance with animal research regulations established by the Animal Welfare Act and Public Health Service.

Plant extracts and steroid-like compounds: A 25% ethanol/water extract of fresh potato sprouts (Solanum Extract, or SE) known to contain the steroid-like glycoalkaloids, solanine, chaconine, demissin (17–20), was prepared from locally obtained plant material and dehydrated by rotary evaporator (Yamato, Japan). The dried SE was dissolved in physiological saline before use.

Solanine and Chaconine were purchased from Sigma Chemical Co. (St. Louis, Mo.). These steroid glycoalkaloids were dissolved in 95% ethanol as stock solutions and stored at $-20°$ C. until used. Just prior to administration, working concentrations of solanine or chaconine were prepared from the stock solutions using a saline diluent. In a few instances, solanine was dissolved in propylene glycol (Sigma, St. Louis, Mo.) shortly before use in specific tests.

Solanidine and diosgenin, which represent the steroid-like portions of the glycoalkaloids minus the oligosaccharides, were obtained from Sigma (St. Louis, Mo.). In preparation for injection, these compounds were dissolved in propylene glycol.

Microbial pathogens: S. typhimurium SL1344 was provided by Dr. David Low (Department of Pathology, University of Utah). The bacteria were grown on Brain-Heart Infusion agar plates to get representative colonies, which were then inoculated into Brain-Infusion broth. The broth was incubated with vigorous shaking at 37° C. When the absorbance reached 1.0 at 600 nm ($\approx 2\times10^9$ microorganisms per 1 ml), the bacteria were pelleted by centrifugation. Quantitation of bacteria was determined using the Brain-Heart Infusion agar plate count technique. The pelleted bacteria were resuspended in PBS and washed 3 times. To determine the $LD_{50}$ of S. typhimurium administered by either the intraperitoneal or oral route, groups of 8 to 10 mice were infected with different numbers of microbes ($10^2$ to $10^{10}$ CFU) i.p. or orally. Animals were observed for 14 days post challenge, and the $LD_{50}$ was evaluated by probit analysis (21, 22).

Preventive treatments of mice: Mice were injected intraperitoneally (i.p.) with 0.1 ml of SE (50 to 200 µg per mouse), solanine (0.1 to 10 µg per mouse), or chaconine (0.1 to 10 µg per mouse in saline at 1 to 14 days before challenge with S. typhimurium SL1344. In some experiments, SE (200 to 1000 µg per mouse) was administered orally by dosing needle to anesthetized mice 5 days prior to challenge. In the experiments designed to compare the relative effectiveness of glycoalkaloids (solanine, 1 µg per mouse) or aglycons (solanidine, 0.5 µg per mouse, and diosgenin, 0.5 µg per mouse), the test substances were dissolved in propylene glycol and injected into inguinal subcutis of mice 5 days prior to bacterial challenge.

Histopathology: Major organs collected from treated and control mice were analyzed for tissue changes after either single or multiple (triple) exposures to solanine or chaconine, given at doses of 1, 5, 25 and 50 µg of glycoalkaloid per mouse. Liver, spleen, kidneys, heart, lungs, and thymus were collected and examined from four animals in each dose group. The organs were trimmed and processed to slides by standard histology methods. Each 5µ section was examined by light microscopy after staining with hermatoxylin and eosin. p Survival assay: Groups of 5 to 10 mice were pre-treated with SE, pure glycoalkaloids (solanine, chaconine) or the aglycons (solanidine, diosgenin) by single or multiple i.p. injections or oral gavage (as described above). Naive control groups for each experiment received saline. All animals were observed daily after challenge with different doses of *S. typhimurium* orally or intraperitoneally. Mortality and weight loss were monitored.

Bacterial clearance assay: An assay was designed to evaluate bacterial clearance at various times faster infection. CF-1 mice received 1 µg of solanine i.p. 1 or 5 days prior to infection. These animals, plus controls, were challenged i.p. with $1 \times 10^6$ CFU of *S. typhimurium*. Three mice were sacrificed at various time points (1, 2, 4 hours post challenge) for analysis of bacterial numbers in selected target organs. Control animals received saline diluent instead of solanine, but were challenged i.p. with the same number of bacterial as the test animals.

Analysis of serum opsonin activity: *S. typhimurium* was incubated for 1 hour at 37° C. in 12% pooled PBS-diluted serum taken from animals previously treated with solanine ("solanine activated" serum). After the incubation period, the bacteria were washed twice, counted, and used for intraperitoneal challenge of naive CF-1 strain mice ($1 \times 10^6$ per mouse). Control mice were challenged with *S. typhimurium* that were pretreated in an identical manner except with 12% serum taken from animals never treated with solanine. Three to four mice were sacrificed at 2 and 4 hours postchallenge for quantitation of *S. typhimurium* in target organs.

Quantitation of *S. typhimurium* in target organs or feces: Five days after bacterial challenge, quantitation of *S. typhimurium* numbers in spleen, liver, and feces of individual CF-1 mice was conducted. All survivors at five days postinfection were sacrificed and pieces of spleen (≈100 mg) or liver (≈500 mg) were removed, homogenized in PBS, and 10-fold serial dilutions seeded into 60 mm Petri dishes of Salmonella-Shigella agar (BBL, Cockeysville, Md.). A single fecal pellet was dissociated in 500 µl of PBS, vortexed, and 10-fold dilutions plated onto agar plates. After 18–24 hours of incubation at 37° C., individual colonies (CFU) were quantitated.

Assay for direct bactericidal, or bacteriostatic effects of glycoalkaloids; *S. typhimurium* was plated on Salmonella-Shigella selective agar plates. Two hours later, SE (50, 500 or 5000 µg per disk) solanine or chaconine (0.5, 5 or 50 µg/disk), or gentamicin (1, 10 µg/disk) as a positive control, were applied onto the plates. After 24 hours incubation, plates were screened to determine bactericidal/bacteriostatic activity of the compounds.

EXAMPLE 2

Intraperitoneal Administration of Solanum Extract Enhances Survival Rate of Infected Animals Extracts prepared from the sprouts of the common potato (*Solanum tuberosum*), a source of the steroid glycoalkaloids, solanine and chaconine, were found to significantly enhance innate immunity following administration to normal experimental animals. In the initial studies, normal male adult mice (CF-1) were treated i.p. with either 50 µg or 200 µg of Solanum extract (SE), prepared from locally obtained plant material. The animals were then challenged orally with 2 $LD_{50}$ of *S. typhimurium* SL1344 either 1 day or 5 days later. At 5 days postinfection, the surviving animals were sacrificed and the number of *S. typhimurium* present in selected organs and feces were quantitated. The results of the initial study are presented in Table 1. Administration of SE prior to challenge increased the survival rate of infected animals to nearly 100%, compared to the 50% survivors remaining in the control group. The liver and spleen of all animals in the groups which received treatment were nearly free of *S. typhimurium* infection, when the SE was given at 50 or 200 µg/mouse 5 days before challenge, or at 200 µg/mouse 1 day before bacterial challenge. The number of *S. typhimurium* in fecal pellets of the SE treated mice at day 5 postinfection was less than 1 percent of that observed in the control group.

TABLE 1

Intraperitoneal Injection Of Normal Adult Mice With SE Increases Survival Rate And Reduces The Level Of Infection In Selected Organs Following Oral Challenge With *S. typhimurium* SL1344

|  | Survival rate[1] (live/total) | Liver Culture (CFU/500 mg) $\times 10^4$ | Spleen Culture (CFU/100 mg) $\times 10^4$ | Fecal Culture (CFU/pellet) $\times 10^4$ |
|---|---|---|---|---|
| Control | 5/10 | 4.0 ± 0.05[2] | 3.2 ± 0.7 | 52.0 ± 5.9 |
| SE 50 µg, d-5[3] | 5/5 | negative | negative | 0.2 ± 0.09 |
| SE 200 µg, d-5 | 5/5 | negative | negative | 0.4 ± 0.1 |
| SE 50 µg, d-1[4] | 4/5 | 0.2 ± 0.2 | 0.15 ± 0.15 | 0.7 ± 0.1 |
| SE 200 µg, d-1 | 5/5 | negative | negative | 0.5 ± 0.2 |

[1]Survival rates were counted 5 days post challenge with *S. typhimurium* ($5 \times 10^7$ CFU).
[2]On day 5 postchallenge the number of *S. typhimurium* present in organs and feces were calculated from the remaining survivors.
[3]SE was administered to animals i.p. (50 or 200 µg per mouse) 5 days before challenge.
[4]SE was administered to animals i.p. (50 or 200 µg per mouse) 1 day before challenge.

EXAMPLE 3

Oral Administration of Solanum Extract Enhances Survival Rate of Infected Animals Experiments were conducted to determine whether SE could be effective when administered by gavage. Groups of normal mice were given SE (200 µg or 1000 µg) 5 days prior to infection. Animals receiving oral SE were totally protected following challenge with 2 $LD_{50}$ of *S. typhimurium*. The treated animals also exhibited a greater than 90% reduction in the number of CFU of *S. typhimurium* present in their spleen, liver and feces at 5 days postinfection compared to the surviving animals from the control group (Table 2).

TABLE 2

Oral Administration Of SE Reduces Susceptibility Of CF1 Mice To Oral Challenge With *S. typhimurium* SL1344

|  | Survival rate[1] (live/total) | Liver Culture (CFU/500 mg) $\times 10^4$ | Spleen Culture (CFU/100 mg) $\times 10^3$ | Fecal Culture (CFU/pellet) $\times 10^4$ |
|---|---|---|---|---|
| Control | 2/5 | 24.0 ± 4.0[2] | 72.0 ± 28.0 | >30.0 |
| SE 200 µg[3] | 5/5 | 0.3 ± 0.1 | 1.2 ± 0.5 | 1.8 ± 0.6 |
| SE 1000 µg[3] | 4/4 | 2.1 ± 0.6 | 9.0 ± 0.6 | 2.9 ± 0.9 |

[1]Survival rates were counted 5 days post challenge with *S. typhimurium* ($5 \times 10^7$ CFU).
[2]On day 5 post challenge the number of *S. typhimurium* present in organs and feces was calculated from the remaining survivors.
[3]SE was administered to animals orally (200 and 1000 µg per mouse) 5 days before challenge.

EXAMPLE 4

Administration of Solanum Extract After Infection Enhances Survival Rate of Infected Animals Experiments were conducted to determine whether SE could be effective when administered subsequent to infection. Groups of normal mice were given SE (200 μg or 1000 μg) either i.p. or orally 1 hour post infection. Animals receiving i.p. or oral SE were protected when the SE was administered 1 hour post infection with 8×10$^7$ CFU of *S. typhimurium*. The treated animals also exhibited a greater than 90% reduction in the number of CFU of *S. typhimurium* present in their spleen, liver and feces at 6 days postinfection compared to the surviving animals from the control group (Table 3).

TABLE 3

Early Treatment of Normal Adult Mice With SE Increases Survival Rate and Reduces the Level of Infection in Selected Organs Following Oral Challenge with *S. typhimurium* SL1344

|  | Survival rate[1] (live/total) | Liver Culture (CFU/500 mg) × 10$^4$ | Spleen Culture (CFU/100 mg) × 10$^3$ | Fecal Culture (CFU/pellet) × 10$^4$ |
|---|---|---|---|---|
| Control | 3/6 | 25.0 ± 9.8[2] | 4.0 ± 0.3 | 25.8 ± 4.7 |
| SE 200 μg[3] | 6/6 | 0.3 ± 0.1 | negative | 0.7 ± 0.1 |
| SE 1000 μg[3] | 5/6 | 0.4 ± 0.06 | 0.2 ± 0.04 | 0.2 ± 0.1 |
| SE 200 μg[4] | 5/6 | 0.1 ± 0.1 | 0.1 ± 0.03 | 0.6 ± 0.2 |
| SE 1000 μg[4] | 5/6 | negative | negative | 0.7 ± 0.2 |

[1]Survival rates were counted 6 days post oral challenge with *S. typhimurium* (8 × 10$^7$ CFU).
[2]On day 6 post challenge the number of *S. typhimurium* present in organs and feces was calculated from the remaining survivors.
[3]SE was administered to animals i.p. (200 or 1000 μg per mouse) 1 hour post infection.
[4]SE was administered to animals orally (200 or 1000 μg per mouse) 1 hour post infection.

EXAMPLE 5

Toxicity Analysis

Solanum extracts contain a number of glycoalkaloids (solanine, chaconine, demissin). Some of these compounds are known to possess toxic properties when administered to animals at high doses (>30 mg/kg). We evaluated the toxicity of solanine and chaconine at a broad range of doses (1 to 50 μg/mouse; 0.03 to 1.7 mg/kg) following single or multiple administrations. No lesions were observed in tissues from any dose group, including the animals given 50 μg (1.7 mg/kg) of either of the glycoalkaloids.

EXAMPLE 6

Analysis of Glycoalkaloid Components on Protective Effect

Because of the known bioactivities of the noted glycoalkaloids, they were analyzed to determine whether any of these substances might be responsive for the observed protection afforded SE treated mice against challenge with *S. typhimurium*. The initial studies evaluated solanine, the primary glycoalkaloid present in SE (50–60% of total glycoalkaloid fraction (18)). The results presented in Table 4 show that a single intraperitoneal injection of solanine at 1.0 μg/mouse was able to enhance the survival of animals receiving an oral challenge with *S. typhimurium* given 5 days after solanine treatment. Furthermore, solanine treatment also reduced the level of infection in the target organs of experimental animals when evaluated 5 days post-infection. Similar results were obtained with chaconine.

TABLE 4

Parenteral Treatment Of Normal Mice With Solanine Protects Them From Oral Challenge With *S. typhimurium* SL1344

|  | Survival rate[1] (live/total) | Liver Culture (CFU/500 mg) × 10$^4$ | Spleen Culture (CFU/100 mg) × 10$^3$ | Fecal Culture (CFU/pellet) × 10$^4$ |
|---|---|---|---|---|
| control | 2/5 | 24.0 ± 4.0[2] | 72.0 ± 28.0 | >30.0 |
| solanine (1 μg d-5[3]) | 5/5 | 0.3 ± 0.1 | 2.0 ± 0.2 | 20.0 ± 3.5 |

[1]Survival rates and organ cultures were counted 5 days post oral challenge with *S. typhimurium* (5 × 10$^7$ CFU).
[2]On day 5 post challenge the number of *S. typhimurium* present in organs and feces were calculated from the remaining survivors.
[3]Solanine was administered to animals i.p. (1 μg per mouse) 5 days before challenge.

EXAMPLE 7

Intraperitoneal Administration of Solanine or Chaconine Reduces Level of Infection with *Candida albicans* Amb 23A Experiments were conducted to determine the level of infection in selected organs of mice challenged with *Candida albicans* Amb 23A. Groups of mice were given solanine or chaconine i.p. every other day to receive three infections. Mice were challenged i.v. with 2×10$^6$ CFU *Candida albicans* Amb 23A the next day after the last injection of glycoalkaloid. The number of microorganisms present in various organs were calculated 24 hours post challenge and the results are shown in Table 5. The results show a reduction in the level of infection in the organs examined.

TABLE 5

Intraperitoneal Injection of Normal Adult Mice with Glycoalkaloids Reduces the Level of Infection in Selected Organs 24 Hours after i.v. Challenge with *Candida albicans* Amb 23A

|  | Liver Culture (CFU/500 mg) × 10$^4$ | Spleen Culture (CFU/100 mg) × 10$^3$ | Fecal Culture (CFU/pellet) × 10$^4$ |
|---|---|---|---|
| Control | 6.2 ± 1.8[1] | 2.2 ± 0.2 | 2.1 ± 0.6 |
| solanine, 1 μg 3x, i.p.[2] | 4.3 ± 0.1 | 0.9 ± 0.06 | 0.1 ± 0.06 |
| chaconine, 1 μg 3x, i.p.[2] | 2.3 ± 0.1 | 0.6 ± 0.02 | 0.02 ± 0.0 |

[1]The number of microorganisms were calculated in the organs 24 hours post i.v. challenge with *Candida albicans* Amb 23 A.
[2]The glycoalkaloid was administered every other day for the three doses.

EXAMPLE 8

Intraperitoneal Administration of Solanine or Chaconine Enhances Survival Rate of animals Infected with *Candida albicans* Amb 23A Experiments were conducted to determine the level of infection in selected organs of mice challenged with *Candida albicans* Amb 23A. Groups of mice were given solanine or chaconine i.p. every other day to receive three infections. Mice were challenged i.v. with 1.8×10$^7$ CFU *Candida albicans* Amb 23A the next day after the last injection of glycoalkaloid. The survival rate and the number of microorganisms present in various organs was calculated in surviving animals 5 days post challenge and the results are shown in Table 5. The results show a reduction in the level of infection in the organs examined.

TABLE 6

Intraperitoneal Injection of Normal Adult Mice with Glycoalkaloids Increases Survival Rate and Reduces the Level of Infection in Selected Organs Following i.v. Challenge with *Candida albicans* Amb 23A

|  | Survival rate[1] (live/total) | Liver Culture (CFU/500 mg) × $10^4$ | Spleen Culture (CFU/100 mg) × $10^3$ | Fecal Culture (CFU/pellet) × $10^4$ |
| --- | --- | --- | --- | --- |
| Control | 4/8 | 3.2 ± 0.3[2] | 2.6 ± 0.9 | 25.8 ± 4.7 |
| solanine, 1 µg 3x, i.p.[3] | 7/8 | 0.4 ± 0.4 | 1.0 ± 0.6 | 0.05 ± 0.02 |
| chaconine, 1 µg 3x, i.p.[3] | 8/8 | 0.9 ± 0.3 | 1.4 ± 1.0 | 0.8 ± 0.3 |

[1]Survival rates were counted 5 days post i.v. challenge with *Candida albicans* Amb 23 A.
[2]The number of microorganisms were calculated in the organs of surviving animals 5 days post i.v. challenge with *Candida albicans* Amb 23 A.
[3]The glycoalkaloid was administered every other day for the three doses.

Examples 2–8 have shown that solanine and chaconine (0.03–0.3 mg/kg body weight [0.1–1.0 µg per mouse]) and low doses of potato sprout extracts containing approximately 1% of the total glycoalkaloid fraction could significantly augment the antimicrobial and antifungal activities of the innate immune system. These doses of solanine and chaconine are 100 to 1000 times lower than the $LD_{50}$ (42 mg/kg) for mice. Experimental animals, whose innate defenses were enhanced by glycoalkaloid treatment, could be rendered capable of withstanding oral or parenteral challenge with lethal doses of enteric microbial pathogens, such as a *S. typhimurium*. Almost all mice treated orally or parenterally (i.p.) with SE or any of the glycoalkaloids 1–5 days before challenge with moderate doses of *S. typhimurium* SL1344 (2 $LD_{50}$) were effectively protected against extensive infection of spleen and liver with a much higher survival rate than the untreated controls. Solanum Extract or pure glycoalkaloids provided more effective protection against *S. typhimurium* than other non-specific immunostimulators used in similar experiments. Indeed, muramyl-dipeptide administered i.p. 1–3 days before challenge with the same microbial dose (2 $LD_{50}$) was able to protect only 50% of the mice (48–50). Mytilan, another non-specific high molecular weight polysaccharide derived from Mydia (sea plant), enhanced survival rates (75–100%) when challenged with 1 $LD_{50}$ dose (51). These data show that solanine and/or chaconine are the chemical entities responsive for augmenting the host's innate immunity, thus providing resistance to infection. The protective properties of SE are also due, mostly, to the presence of solanine and/or chaconine. Similar effects were seen against the fungus *Candida albicans* Amb 23A.

EXAMPLE 9

Comparison of Activity of Glycoalkaloid with Aglycon

Plant glycoalkaloids consist of the aglycon portion, which is structurally similar to a typical steroid molecule, coupled to an oligosaccharide moiety of defined structure. Solanine and chaconine posses the same aglycon, solanidine, which is bound to distinct oligosaccharides. Solanine, solanidine, and diosgenin, another aglycon which is slightly different than solanidine, were evaluated for their capacity to enhance host resistance to bacterial infection. Data presented in Table 7 show, that only solanine was able to effectively protect mice against the bacterial infection. Similar activity was seen for chaconine. Neither solanidine nor diosgenin possessed any protective activity against infection with *S. typhimurium*.

TABLE 7

Glycoalkaloid Solanine Only, But Not Aglycons, Can Effectively Protect Normal Mice Against *S. typhimurium* SL1344

|  | Survival rate[1] (live/total) | Liver Culture (CFU/500 mg) × $10^6$ | Spleen Culture (CFU/100 mg) × $10^6$ |
| --- | --- | --- | --- |
| control | 6/10 | 3.9 ± 1.2 | 4.5 ± 0.8 |
| solanine 1 µg[2] | 9/10 | 0.8 ± 0.5 | 0.8 ± 0.5 |
| solanidine 0.5 µg[2] | 3/10 | 5.3 ± 2.4 | 1.7 ± 0.6 |
| diosgenin 0.5 µg[2] | 4/10 | 8.5 ± 3.3 | 4.8 ± 1.8 |

[1]Survival rates and organ cultures were counted 5 days post i.p. challenge with *S. typhimurium* SL1344 (1.2 × $10^3$ CFU (8 $LD_{50}$)).
[2]Solanine (1 µg/mouse), solanidine (0.5 µg/mouse) or diosgenin (0.5 µg/mouse) were administered to animals inguinal pocket 5 days before challenge.

These results show that both portions of the glycoalkaloid molecule, aglycon and oligosaccharide, were critically important in increasing survival and reducing infection in target organs. These results suggest that the protective effects of glycoalkaloids may be related somehow to activation of cellular membranes by the oligosaccharide component of these molecules. Indeed, a group of researchers from the Netherlands employed techniques of model- and bio-membranes to establish that the sugar moiety plays a central role in glycoalkaloid-membrane interactions (52, 53). The steroid aglycons or free sugars did not show membrane affinity as high as the molecules of glycosides (52, 53).

EXAMPLE 10

Protection Against high Bacterial Dose with Single Administration of Glycoalkaloid The magnitude of microbial exposure which can be tolerated by a host under various conditions is always of interest to health professionals. The above results demonstrate that a low dose of solanine or chaconine induced tolerance to moderate quantities (2–8 $LD_{50}$) of *S. typhimurium* SL1344. In view of these results, studies were conducted in which higher doses of bacteria were administered.

Figure 1B:
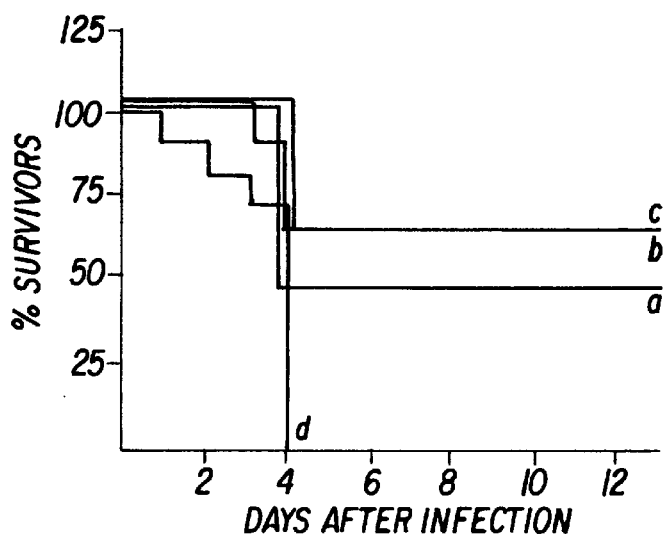
FIG. 1B. Lifespan monitoring of normal adult mice pretreated with solanine and challenged intraperitoneally with 25 $LD_{50}$ of S. typhimurium. Each group of 10 mice was given solanine i.p. 7 days before challenge at the indicated doses: (a) 0.1 μg per mouse; (b) 1.0 μg per mouse; (c) 10.0 μg per mouse; (d) naive controls received only saline.
Figure 1C:
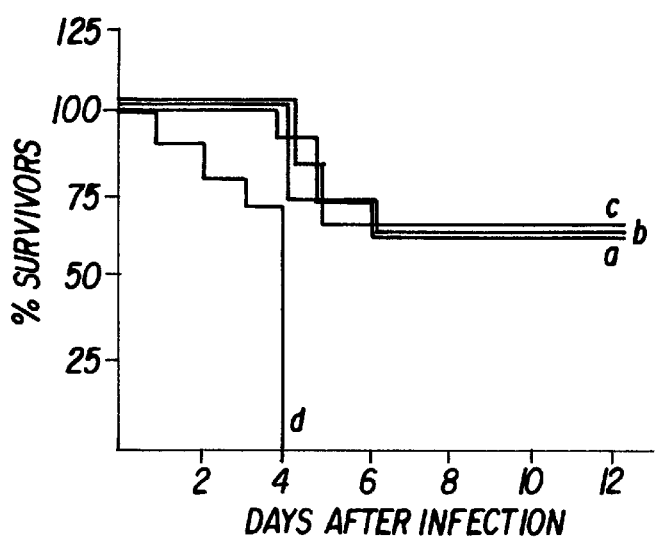
FIG. 1C. Lifespan monitoring of normal adult mice pretreated with solanine and challenged intraperitoneally with 25 $LD_{50}$ of S. typhimurium. Each group of 10 mice was given solanine i.p. 1 day before challenge at the indicated doses: (a) 0.1 μg per mouse; (b) 1.0 μg per mouse; (c) 10.0 μg per mouse; (d) naive controls received only saline.

A single low dose of solanine prior to bacterial challenge provided protection against a moderate dose of *S. typhimurium*. This led to question whether glycoalkaloid treatment could also provide protection to mice that received a high dose of *S. typhimurium* (25 $LD_{50}$). Treatment of normal mice with a single 1 µg dose of solanine or chaconine, the other major glycoalkaloid present in potato sprouts, five days prior to bacterial challenge resulted in a survival rate of approximately 40% for solanine and 75% for chaconine. However, all untreated control animals were dead or agonal (Table 8) by day 4 post infection. Experiments were also conducted to determine the optimal dose of glycoalkaloid for animal treatment, and to determine the duration of enhanced resistance to bacterial infection. Groups of mice were treated with solanine at doses of 0.1, 1.0, or 10.0 µg. Animals from each treatment group were challenged with *S. typhimurium* 1, 7, or 14 days later. The results (FIG. 1) demonstrate that a single administration of glycoalkaloid at any of the dosages tested was able to enhance resistance to infection in 40–70% animals. At the higher dosages (1.0 and 10.0 µg), the enhanced host resistance afforded by a single treatment with solanine appeared to last for at least 2 weeks.

TABLE 8

Treatment Of Normal Adult Mice With Glycoalkaloids Increases Survival Rate And Reduces The Level Of Infection In Selected Organs Following I.P. Challenge With *S. typhimurium* SL 1344

|  | Survival rate[1] (live/total) | Liver Culture (CFU/500 mg) × $10^6$ | Spleen Culture (CFU/100 mg) × $10^6$ |
| --- | --- | --- | --- |
| control | 0/8[2] | 5.2 ± 0.3 | 3.4 ± 0.3 |
| solanine 1, i.p.[3] | 3/8 | 1.4 ± 0.2 | 0.7 ± 0.1 |
| chaconine 1, i.p.[3] | 6/8 | 1.8 ± 0.3 | 0.9 ± 0.1 |

[1]Survival rates and organ cultures were counted 5 days post i.p. challenge with *S. typhimurium* SL 1344 (4 × $10^3$ CFU).
[2]Most mice in the naive control group (received saline) were dead by day 4 after challenge, whereas two terminally ill survivors were sacrificed on day 5 for organ culture.
[3]Solanine or chaconine were administered to animals i.p. (1 µg per mouse) 5 days before challenge.

EXAMPLE 11

Protection Against High Bacterial Dose with Multiple Administrations of Glycoalkaloid The remarkable efficacy of glycoalkaloids in protecting against the effects of bacterial infection encouraged us to explore treatment regimes that would prevent death in all the animals challenged with high doses of *S. typhimurium*. Therefore, it was suggested that multiple administrations of glycoalkaloid might serve to further enhance the level of antimicrobial resistance. Mice were provided an intraperitoneal treatment of glycoalkaloid at 1 µg/dose once every other day for 6 days prior to being challenged with a lethal dose (25 $LD_{50}$) of *S. typhimurium*. The data presented in Table 9 shows that mice given solanine, chaconine or a mixture of both alkaloids, were rendered highly resistant to challenge with *S. typhimurium*. All of the glycoalkaloid treated animals were alive 5 days after infection, and showed no signs of illness or weight loss during a 12 day observation period. Most of the control mice which received injections of saline died by day 4 postinfection. Three animals from each treatment group, and the three agonal survivors from the control group, were sacrificed for analysis of selected organs on day 5 post challenge. This study revealed that the livers and spleens of animals in the glycoalkaloid treated groups were almost totally free of *S. typhimurium* infection, while the organs from the remaining control animals were highly infected.

TABLE 9

Multiple Treatment Of Normal Adult Mice With Glycoalkaloids Increases Survival Rate And Significantly Reduces The Level Of Infection In Selected Organs Following I.P. Challenge With *S. typhimurium* SL1344

|  | Survival rate[1] (live/total) | Liver Culture (CFU/500 mg) × $10^6$ | Spleen Culture (CFU/100 mg) × $10^6$ |
| --- | --- | --- | --- |
| control | 0/8[2] | 6.1 ± 0.9 | 2.4 ± 0.5 |
| solanine 1 µg[3] | 8/8 | 0.08 ± 0.07[4] | 0.08 ± 0.02[4] |
| chaconine 1 µg[3] | 8/8 | 0.12 ± 0.09[4] | 0.03 ± 0.01[4] |
| solanine 0.5 µg + chaconine 0.5 µg[5] | 8/8 | 0.08 ± 0.08[4] | 0.08 ± 0.08[4] |

[1]Survival rates and organ cultures were counted 5 days post i.p. challenge with *S. typhimurium* SL1344 (3.5 × $10^3$ CFU).

TABLE 9-continued

Multiple Treatment Of Normal Adult Mice With Glycoalkaloids Increases Survival Rate And Significantly Reduces The Level Of Infection In Selected Organs Following I.P. Challenge With *S. typhimurium* SL1344

|  | Survival rate[1] (live/total) | Liver Culture (CFU/500 mg) × $10^6$ | Spleen Culture (CFU/100 mg) × $10^6$ |
| --- | --- | --- | --- |

[2]Most mice in the naive control group (received saline) were dead by day 4 after challenge, whereas the three last terminally ill survivors were sacrificed on the day 5 for organ culture.
[3]Solanine or chaconine were administered together to animals i.p. (0.5 µg per mouse) 3 times every other day before challenge.
[4]Difference between control and solanine pretreated mice was significant (p < 0.001) analyzed by ANOVA for multiple datasets with statistical software Statview (version 4.01).
[5]Solanine and chaconine were administered i.p. together to animals (0.5 µg per mouse of each) 3 times every other day before challenge.

Examples 10 and 11 demonstrate that sixty to a hundred percent of the animals were protected against massive doses (25 $LD_{50}$, i.p.) of *S. typhimurium* SL1344 when they were given a single or multiple injections of solanine or chaconine. In addition to preventing death, the glycoalkaloids greatly reduced the number of organisms recovered from liver and spleen. In these studies, the survivors were observed for 12 day while all of the control mice were dead by post-injection day four. Protection offered by a single dose of glycoalkaloid is comparable to that produced by antigen specific vaccines against *S. typhimurium* administered in high doses (70 to 90% survivors) (54, 55). Multiple (triple) administrations of solanine or chaconine (every other day before challenge) led to dramatic improvement in the survival rate, as well as almost complete clearance of infection from organs.

All experiments present in Examples 2–11 were repeated at least 3 times. Statistical analysis was determined by Student's t-test (p<0.001), and each value was given as the mean±S.D.

EXAMPLE 12

Intraperitoneal Administration of Glycoalkaloids Enhances Survival Rate of Infected Animals Similar experiments were conducted to determine the protective effect of Solanum extract on mice infected with other microbes. In these experiments, a total fraction of glycoalkaloids (solanine, chaconine and minor glycoalkaloids) was separated from Solanum extract by an extraction with 2% sulfuric acid followed by an extraction with ethanol. The glycoalkaloids were administered intraperitoneally to CF-1 mice (0.1–10 µg/mouse) 1 or 7 days prior to challenge with live microorganisms. Naive mice (control received the same volume of saline (100 µl). In the first experiment, mice were challenged with a lethal dose of *Francisella tularensis* strain Guysky, specifically 10 $LD_{50}$ (500 microbes/mouse). In the second experiment, mice were challenged with a sublethal dose of *Pseudomonas aeruginosa* strain 20, specifically 1 $LD_{50}$ ($10^5$ CFU/mouse). In the third experiment, mice were challenged with a lethal dose of *Pseudomonas aeruginosa* strain 20, specifically 10 $LD_{50}$. Survivors were monitored daily, and the survival rate was counted at day 14 post challenge for the first experiment and at day 7 post challenge for the second and third experiment. The results of these experiments are shown in Tables 10–12.

TABLE 10

Pretreatment with Glycoalkaloids Protected Normal
Mice Against Lethal Challenge with *Francisella tularensis*

|  | Dose of alkaloids (μg/mouse) | Survival Rate on Day 14 Post Challenge |
| --- | --- | --- |
| naive control | 0.0 | 0/10 |
| glycoalkaloids 1 day pre-challenge | 0.1 | 4/10 |
|  | 1.0 | 5/10 |
|  | 10.0 | 4/10 |
| glycoalkaloids 7 day pre-challenge | 0.1 | 3/10 |
|  | 1.0 | 4/10 |
|  | 10.0 | 4/10 |

TABLE 11

Pretreatment with Glycoalkaloids Protected Normal Mice
Against Sublethal Challenge with *Pseudomonas aeruginosa*

|  | Dose of alkaloids (μg/mouse) | Survival Rate on Day 7 Post Challenge |
| --- | --- | --- |
| naive control | 0.0 | 6/12 |
| glycoalkaloids 1 day pre-challenge | 0.1 | 6/10 |
|  | 1.0 | 7/10 |
|  | 10.0 | 10/10 |
| glycoalkaloids 7 day pre-challenge | 0.1 | 8/10 |
|  | 1.0 | 8/10 |
|  | 10.0 | 9/10 |

TABLE 12

Pretreatment with Glycoalkaloids Protected Normal
Mice Against Lethal Challenge with *Pseudomonas aeruginosa*

|  | Dose of alkaloids (μg/mouse) | Survival Rate on Day 7 Post Challenge |
| --- | --- | --- |
| naive control | 0.0 | 0/20 |
| glycoalkaloids 1 day pre-challenge | 0.1 | 2/10 |
|  | 1.0 | 4/10 |
|  | 10.0 | 4/10 |
| glycoalkaloids 7 day pre-challenge | 0.1 | 3/10 |
|  | 1.0 | 7/10 |
|  | 10.0 | 9/10 |

The results show that a single prophylactic treatment with different doses of glycoalkaloids was able to protect a part of the mice (30–50%) against lethal infection with *Fr. tularensis*, whereas the naive controls were all dead. Similarly, this treatment partially or completely protected mice from infection with *Ps. aeruginosa* in a sublethal challenge, whereas 50% of the naive controls were dead by day 5 post challenge. Finally, this treatment protected mice from infection with *Ps. aeruginosa* in a lethal challenge with a time- and dose-dependent effect, whereas all of the naive controls were dead by day 2 post challenge.

EXAMPLE 13

Intraperitoneal Administration of Solanum Extract Enhances Survival Rate of Infected Animals In view of the results obtained with mice, an initial study was conducted to determine the protective effect of Solanum extract on pigs against infection by *Salmonella chloeraesuis* strain 370. In this study, one group of 3 baby pigs (13–15 days old, weight 3–7 pounds) was administered SE (100 μg/kg) by intraperitoneal infection 10 days before lethal challenge with the microbes (2×10$^7$ microorganisms/animal). A second group of 2 baby pigs were administered SE (1000 μg/kg) orally with drinking water 10 days before challenge. The control group of 3 pigs were administered saline by intraperitoneal injection and received regular water. Survivors were monitored daily, and the survival rate was counted at day 21 post challenge. The results are shown in Table 10. All control animals died on day 3 or 4 after a lethal challenge, whereas all the pretreated baby pigs survived the Salmonella infection.

TABLE 13

Pretreatment with Solanum Extract Protected Normal
Pigs Against Lethal Challenge with *Salmonella choleraesuis*

|  | Dose of alkaloids (μg/mouse) | Survival Rate on Day 21 Post Challenge |
| --- | --- | --- |
| naive control | 0.0 | 0/3 |
| SE, ip | 100 | 3/3 |
| SE, oral | 1000 | 2/2 |

EXAMPLE 14

Analysis of Mechanism of Action

Figure 2A:
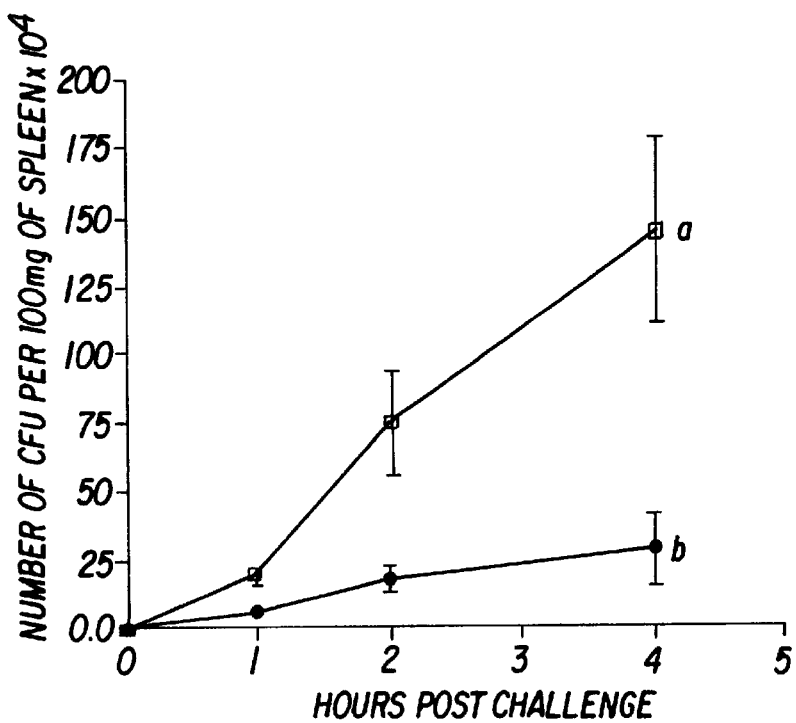
FIG. 2A. CF-1 mice pretreated with solanine 5 days before an intraperitoneal challenge with S. typhimurium SL1344 are able to rapidly clear microorganisms from the spleen; normal control mice (a) or solanine pretreated mice (b) were challenged with $10^6$ CFU/mouse.
Figure 2B:
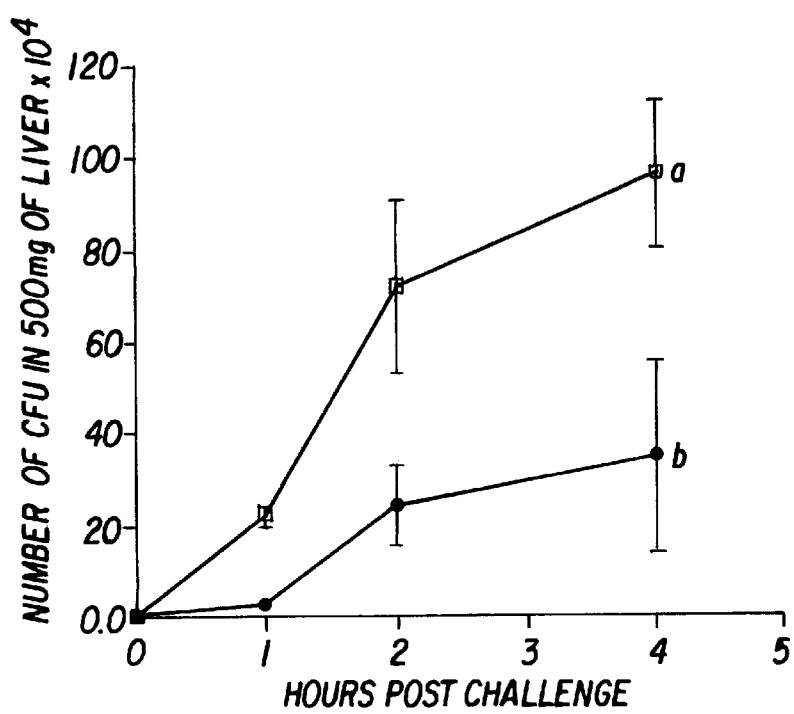
FIG. 2B. CF-1 mice pretreated with solanine 5 days before an intraperitoneal challenge with S. typhimurium SL1344 are able to rapidly clear microorganisms from the liver; normal control mice (a) or solanine pretreated mice (b) were challenged with $10^6$ CFU/mouse.
Figure 3A:
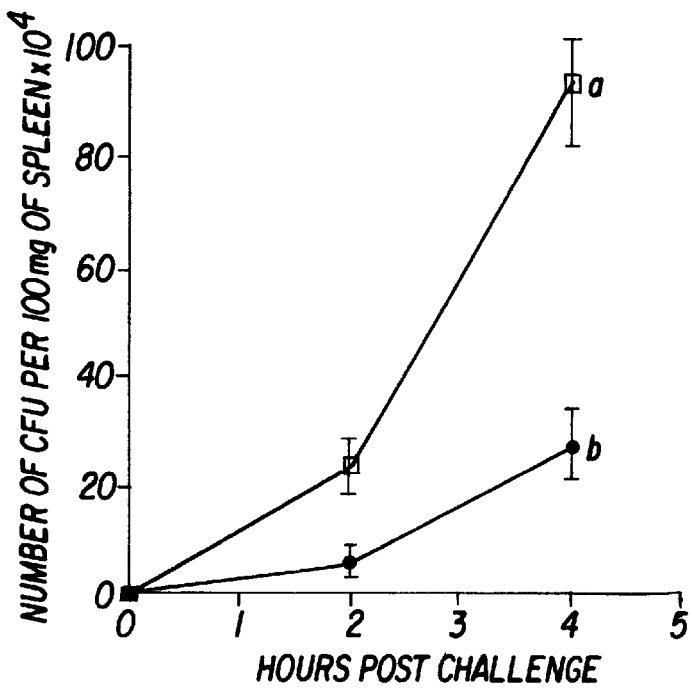
FIG. 3A. Enhanced clearance of S. typhimurium SL1344 from the spleen following a pre-incubation of the microorganisms with serum from solanine-treated animals. S. typhimurium were pre-incubated with either normal murine serum (a) or serum from solanine pretreated animals (b) prior to challenge of naive mice ($10^6$ CFU/mouse) by i.p. injection.
Figure 3B:
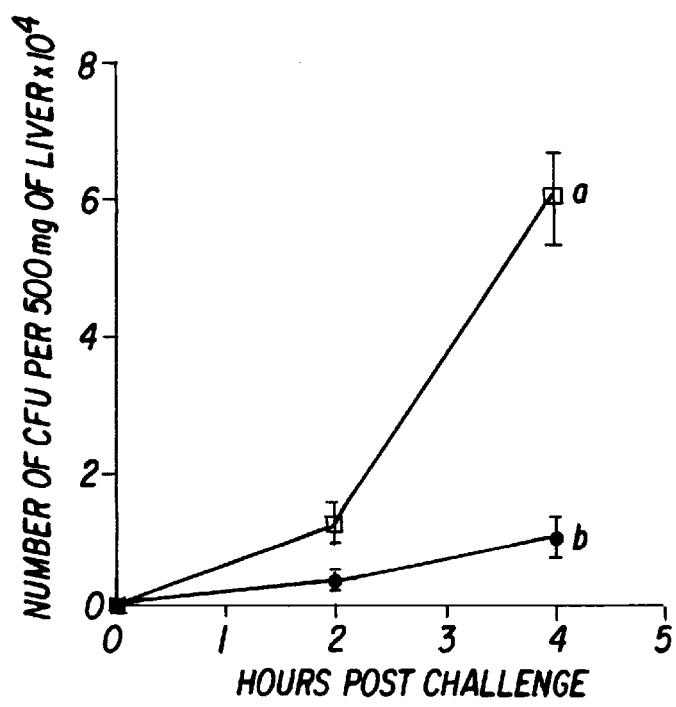
FIG. 3B. Enhanced clearance of S. typhimurium SL1344 from the liver following a pre-incubation of the microorganisms with serum from solanine-treated animals. S. typhimurium were pre-incubated with either normal murine serum (a) or serum from solanine pretreated animals (b) prior to challenge of naive mice ($10^6$ CFU/mouse) by i.p. injection.

Studies designed to define the mechanism(s) responsible for the protective actions of glycoalkaloids determined that mice pretreated with 1 μg of solanine 5 days before an intraperitoneal challenge with a very large dose of *S. typhimurium* possessed far fewer bacteria in their livers and spleens at 1, 2, and 4 hours postchallenge than did controls (FIG. 2). Similar results were obtained when animals received an intraperitoneal treatment with solanine 1 day before microbial infection. Solanine, chaconine, and serum from solanine pretreated animals were found to be neither bactericidal nor bacteriostatic for *S. typhimurium* in vitro. However, injected *S. typhimurium* were rapidly cleared from mouse target organs when the bacteria were incubated prior to injection with serum taken from solanine treated animals (FIG. 3). Pretreatment of *S. typhimurium* with serum from normal naive mice was used as the control. These results suggest that something present in serum of solanine-treated animals is able to effectively opsonize the microbes and facilitate phagocytosis.

The above examples indicate that nonspecific stimulation of innate immunity, considered by some to be of minor importance, produces protection which is comparable to antibiotic and vaccine therapy against bacterial infection. This discovery is highly important in light of predictions by microbiologists and immunologists that the "post-antibiotic era" will come in the early 21st century (1–8). Worldwide bacteria with very high genomic and mutability characteristics continue to develop resistance despite the development of new antibacterial and bacteriostatic agents. Also, an antibacterial strategy employing specific vaccines does not provide control of some infectious diseases. Antigenic variations, highly infective microbes, and the existence of numerous hosts have always hampered the development of new vaccines since the discovery of the first vaccine over two hundred years ago. In view of this, an alternative approach relying on enhancement of innate immune defense mechanisms, which are as effective or more so than vaccines and antibiotics, is extremely important. The strategy of stimulating the host's natural immunity eliminates the problem of bacterial resistance to antibiotics and lack of vaccine specificity.

It is commonly known that some individuals become ill after injecting only a few microbes, while others may consume a thousand times more organisms without any illness (56, 57). This resistance is natural, rather than acquired, since individuals possessing it have no immunoglobulin to specific infectious agents in their blood. Individuals with this trait have a genetic predisposition for it and are naturally resistant to infections because of highly efficient innate immune system. The above examples show that natural immune defense mechanisms of most individuals can be enhanced by treatment with agents like solanine or chaconine, facilitating removal of organisms which may be antibiotic resistant. Although all of the mechanisms triggered in the host's body after glycoalkaloid administration have not been determined, early events following challenge is glycoalkaloid treated hosts have been studied. Bacterial levels in selected organs have been evaluated at 1, 2, and 4 hour after i.p. challenge of mice with a high dose of S. typhimurium SL 1334 ($1 \times 10^6$/mouse). All mice which received solanine 5 days or 1 day prior to bacterial challenge possessed enhanced capacity to reduce bacterial load in the spleen and liver. One hour post challenge, organs of treated animals had fewer microorganisms than controls. It was found that the response to microbes which results in their rapid clearance from organs is due to an enhanced rate of phagocytosis. It was also determined that removal of microorganisms from organs was enhanced if the bacteria were pre-incubated with serum collected form solanine treated animals prior to challenge of naive mice. Similar results were seen when mice were challenged with other microbes and were seen for pigs challenged with Salmonella choleraesuis.

In the above studies it was also observed that there are high molecular weight compounds that might serve as accessory molecules for low molecular weight compounds, the combination of which contributes to the immunomodulary effects, as in Echinacea extracts (26–28). Without being bound by any mechanism of action, it is theorized that high molecular weight proteoglycans in Solanum extract might bind the glycoalkaloids and release them in the host's body over an extended period of time providing a longer-term protection.

In summary, the above data describes an effective approach to protect individuals against bacterial infections and disease. This approach is based on the ability of glycoalkaloid treatment to augment the host's innate immune system. Such an augmentation can efficiently control bacterial growth after infection. The protection of individuals against diseases caused by bacterial infection indicate that the steroid glycoalkaloids from the common potato possess the capacity to enhance host innate defenses. Although the plant-derived glycoalkaloids enhanced the innate immune response and hence are antimicrobial, the above studies confirmed that the glycoalkaloids, including solanine and chaconine, did not possess antibiotic properties.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiment are illustrative and should not be construed as restrictive.

LIST OF REFERENCES

1. Cohen M L. Epidemiology of drug resistance: Implications for a post-antimicrobial era. Science 1992; 257:1050–1055.
2. Neu H C. The crisis in antibiotic resistance. Science 1992; 257:1064–1073.
3. Stone R. Search for sepsis drugs goes on despite past failures. Science 1994; 264:365.
4. Travis J. Reviving the antibiotic miracle? Science 1994; 264:360–362.
5. Davies J. Inactivation of antibiotics and dissemination of resistance genes. Science 1994; 264:375–382.
6. Nikaido H. Prevention of drug access to bacterial targets: permeability barriers and active efflux. Science 1994; 264:382–388.
7. Spratt B. Resistance to antibiotics mediated by target alterations. Science 1994; 264:388–393.
8. Davies J. Bacteria on the rampage. Nature 1996; 383:219–220.
9. Pie S, Matsiota-Bernard P, Truffa-Bachi P, Nauciel C. Gamma interferon and interleukin-10 gene expression in innately susceptible and resistant mice during the early phase of Salmonella typhimurium infection. Infect Immun 1996; 64:849–854.
10. Castro A G, Minoprio P, Appelberg R. The relative impact of bacterial virulence and host genetic background on cytokine expression during Mycobacterium avium infection of mice. Immunol 1995; 85:556–561.
11. Teixeira H, Kaufmann S H E. NK1+ cells are early IFN-gamma producers but impair resistance to Listeria monocytogenes infections. J Immunol 1994; 152:1873–1882.
12. Rest R F, Liu J, Talukdar R, Frangipane J V, Simon D. Interaction of pathogenic Neisseria with host defenses. What happens in vivo? Ann NY Acad Sci 1994; 730:183–196.
13. Mills K H M, Barnard A, Watkins J, Redhead K. Cell-mediated Immunity to Bordetella pertussis: role of Th1 cells in bacterial clearance in murine respiratory infection model. Infect Immun 1993; 61:399–410.
14. Louie A, Baltch A L, Smith R P, et al. Tumor necrosis factor-alpha has a protective role in a murine model of systemic candidiasis. Infect Immun 1994; 62:2761–2772.
15. Tripp C S, Wolf S F, Unanue E R. Interleukin-12 and tumor necrosis factor-alpha are costimulators of interferon gamma production by natural killer cells in severe combined immunodeficiency mice with listeriosis, and interleukin-10 is a physiologic antagonist. Proc Natl Acad Sci 1993; 90:3725–3729.
16. Spaccapel R, Romani L, Tonnetti L, et al. TGF-beta is important in determining the in vivo patterns of susceptibility of resistance in mice infected with Candida albicans. J Immunol 1995; 155:1349–1360.
17. Uppal D S. Varietal and environmental effect on the glycoalkaloid content of potato (Solanum tuberosum L.). Plant Foods Hum Nutr 1987; 37:333–340.
18. Slanina P. Solanine (glycoalkaloids) in potatoes: toxicological evaluation. Food Chem Toxicol 1990; 28:759–761.
19. 1993. Solanine and chaconine. WHO, 339–372. FAO-and-WHO-working groups; Vol 30.
20. Budavari S, O'Neil M J, Smith A, Heckelman P E, ed. 1989. The Merck Index. An Encyclopedia of Chemicals, Drugs and Biologicals. Eleventh ed. Merck and Co, Inc.,
21. Finney D J. 1971. Probit Analysis, Cambridge University Press, 333.
22. Sakakibara T, Ito K, Irie Y. Toxicological studies of bestatin. Acute toxicity test in mice, rats and dogs. JPN J Antibiot 1983; 36:297129–84.
23. 1995. The United States Pharmacopeia. Rockville, Md.: USA Pharmacopeiae Convention, Inc. 1650.
24. Balick M J, Cox P A, 1996. Plant, people and Culture. The Science of Ethnobotany. Basingstoke, N.Y.: Sci Am Library, 228.

25. Tyler V E. 1994. Herbs of Choice. The Therapeutic Use of Phytomedicinals. Pharm Products Press, 186.
26. Haas H. 1991. Arzneipflanzenkunde B. I. Mannheim, Germany: Wissenshaftsverlag, 133–136.
27. 1989. Echinacea Purpurea Leaf. Monographs for Phytomedicines. Bonn, Germany: German Ministry of Health, 102.
28. Foster S. 1991. Nature's Immune Enhancer. Rochester, V T: Healing Art Press, 150.
29. Marty J, Hine A. 1995. The Alternative Health and Medicine Encyclopedia. Detroit: Gale Research Press, 91.
30. Friedman M, Dao L. Distribution of glycoalkaloids in potato plants and commercial potato products. J. Agric Food Chem 1992; 40:419–423.
31. Friedman M, Henika P R. Absence of genotoxicity of potato alkaloids alpha-chaconine, alpha-solanine and solanidine in the Ames Salmonella and adult and foetal erythrocyte micronucleus assays. Food Chem Toxicol 1992; 30:689–694.
32. Hellenas K E, Nyman A, Slanina P, Loof L, Gabrielson J. Determination of potato glycoalkaloids and their aglycon in blood serum by high performance liquid chromatography. J Chromatogr 1992; 573:69–78.
33. Hellenas K E, Cekan E, Slanina P, Bergman K. Studies of embryotoxicity and external malformations after continuous intravenous infusion of alpha-chaconine in pregnant rats. Pharmacol & Toxicol 1992; 70:381–383.
34. Friedman M, Henika P R, Mackey B E. Feeding of potato, tomato and eggplant alkaloids affects food consumption and body and liver weights in mice. J Nutr 1996; 126:989–999.
35. Renwick J N, Clarigbold W D B, Earthy M E, Few J D, McLean A C. Neural-tube defects produced in Syrian hamsters by potato glycoalkaloids. Teratology 1984: 30:371–381.
36. Phillips B J, Hughes J A, Phillips J C, Walters D G, Anderson D, Tahourdin C S M. A study of the toxic hazard that might be associated with the consumption of green potato tops. Food Chem Toxicol 1996; 34:439–448.
37. Wang X O. Teratogenic effect of potato glycoalkaloids. Chung Hua Fu Chan Ko Tsa Chih 1993; 28:73–75, 121–122.
38. Jadhav S J, Sharma R B, Salunkhe D K. Naturally occuring toxic alkaloids in foods. CRC Crit Rev Toxicol 1981; 9:21–104.
39. Johnson H, Hellenas K E. Glycoalkaloids in potato. Var Foda 1983; 35:299–314.
40. Morris S C, Lee T H. The toxicity of teratogenecity of Solanaceae glycoalkaloids, particularly of the potato (*Solanum tuberosum*): a review. Food Technol Aust 1984; 36:118–124.
41. Baker D C, Keeler R F, Garfield W P. Mechanism of death in Syrian hamsters gavaged potato sprout material. Toxicol Pathol 1988; 16:333–339.
42. Cadwell K A, Grosjean O K, Henika P R, Friedman M. Hepatic ornithine decarboxylase induction by potato glycoalkaloids in rats. J Chem Toxicol 1991; 29:531–535.
43. Thorne H V, Clarke G F, Skuce R. The inactivation of Herpes simplex virus by some Solanaceae glycoalkaloids. Antiviral Res 1985; 5:335–343.
44. Sinden S L, Goth R W, O O Brien M J. Effects of potato alkaloids on the growth of *Alternaria solani* and their possible role as resistance factors in potatoes. Phytopathology 1973; 63:3033–07.
45. Fewell A M, Roddick J C, Weissenberg M. Interactions between the glycoalkaloids solasonine and solamargine in relation to inhibition of fungal growth. Phytochemistry 1994; 37:1007–1011.
46. Costs S D, Gaugler R R. Sensitivity of *Beauveria bassiana* to solanine and tomatine: plant defensive chemicals inhibit an insect pathogen. J Chem Ecol 1989; 15:697–706.
47. Zinkevich E P, Vecherko L P. Triterpenoid glycosides (saponins). Annals of the Institute of Medicinal Plants, Moscow, Russia 1968; 13:34–45.
48. Parant M A, Audibert F M, Chedid L A, et al. Immunostimulant activities of a lipophilic muramyl dipeptide derivative and desmuramyl peptolipid analogs. Infect Immun 1980; 27:826–831.
49. Chedid L A, Parant M A, Audibert F M, et al. Biological Activity of a new synthetic muramyl peptide adjuvant devoid of pyrogenicity. Infect Immun 1982; 35:417–424.
50. Parant M A, Parant F J, Le Contel C, P. L, Chedid L. MDP—derivatives and resistance to bacterial infections in mice. Adv Exp Med Biol 1992; 319:175–184.
51. Zaporozhets T S, Ovodova R G, Loenko I N, Besednova N N. Non-specific stimulation of resistance with mytilan—a polysaccharide isolated from the mussel *Crenomytilus grayanus*. Zh Mikrobiol Epidemiol Immunobiol 1981; 9:106–107.
52. Keukens E A J, de Vrije T, van der Boom C, et al. Molecular basis of glycoalkaloid-induced membrane disruption. Biochim Biophys Acta 1995; 1240:2162–28.
53. Keukens E A J, de Vrije T, Jansen L A, et al. Glycoalkaloids selectively permeabilize cholesterol containing biomembranes. Biochim Biophys Acta 1996; 1279:243–250.
54. Saxena M, Di Fabio J L. Salmonella typhi O-polysaccharide-tetanus toxoid conjugated vaccine. Vaccine 1994; 12:879–884.
55. Ding H F, Nakoneczna I, Hsu H S. Protective immunity induced in mice by detoxified salmonella lipopolysaccharide. J Med Microbiol 1990; 31:95–102.
56. Malo D, Skamone E. Genetic control of host resistance to infection. Trends Genet 1994; 10:365–371.
57. Shaw M A, Davies C R, Llanos-Cuentas E A, Collins A. Human genetic susceptibility and infection with *Leishmania peruviana*. Am J Hum Genet 1995; 57:1159–1168.

What is claimed is:

1. A method for enhancing an innate immune response in an individual which comprises administering to the individual an amount of a plant-derived immunomodulator effective to increase the activity of an innate immune defense mechanism in the individual upon infection by an infectious agent, wherein the plant-derived immunomodulator has the formula $$R-R^1,$$

wherein R is a mono- or oligo-saccharide which may optionally be modified with pharmacologically acceptable esters or pharmacologically acceptable ethers, $R^1$ is an aglycon or derivative having the general formulae:

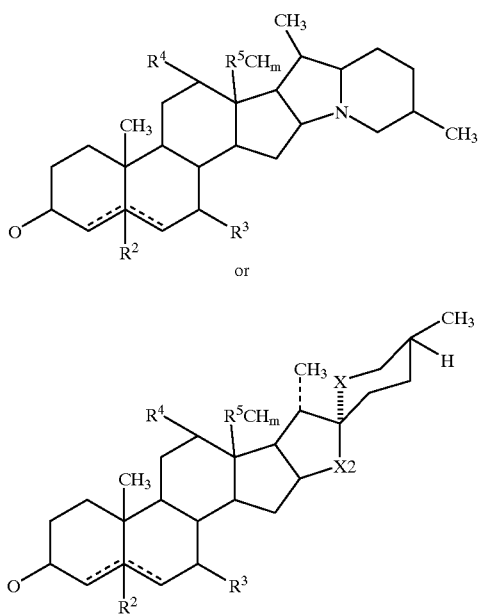

wherein
R² is H when neither of the dashed lines is a double bond or is nothing when one of the dashed lines is a double bond;

R³, R⁴ and R⁵ are independently H, OH, =O, pharmacologically acceptable esters or pharmacologically acceptable ethers;

X and X2 are independently N or O; and m is 1 or 2.

2. The method of claim 1, wherein the plant-derived immunomodulator is selected from the group consisting of a plant containing the immunomodulator, plant tissue containing the immunomodulator and a plant extract containing the immunomodulator and wherein the plant from which the immunomodulator is derived is selected from the group consisting of Solanum species, Veratrum species and Liliaceae species.

3. The method of claim 2, wherein the plant-derived immunomodulator is a plant extract comprising 0.1% to 10% immunomodulator.

4. The method of claim 3, wherein the plant-derived immunomodulator is a plant extract comprising 1% to 5% immunomodulator.

5. The method of claim 3, wherein the plant-derived immunomodulator is a plant extract comprising 1% glycoalkaloids.

6. A method for enhancing an innate immune response in an individual which comprises administering to the individual an amount of a plant-derived immunomodulator effective to increase the activity of an innate immune defense mechanism in the individual upon infection by an infectious agent, wherein the plant-derived immunomodulator is solanine.

7. A method for enhancing an innate immune response in an individual which comprises administering to the individual an amount of a plant-derived immunomodulator effective to increase the activity of an innate immune defense mechanism in the individual upon infection by an infectious agent, wherein the plant-derived immunomodulator is chaconine.

8. The method of claim 1, wherein the plant-derived immunomodulator is a mixture of solanine and chaconine.

9. The method of claim 3, wherein the amount of the plant extract is from about 1.7 mg/kg to 33.5 mg/kg.

10. The method of claim 3, wherein the amount of the plant extract is from about 5 mg/kg to 15 mg/kg.

11. The method of claim 3, wherein the amount of the plant extract is from about 6.5 mg/kg to 10 mg/kg.

12. The method of claim 1, wherein the amount of plant-derived immunomodulator is from about 0.01 mg/kg to 3.0 mg/kg.

13. The method of claim 1, wherein the amount of plant-derived immunomodulator is from about 0.03 mg/kg to 1.0 mg/kg.

14. The method of claim 1, wherein the amount of plant-derived immunomodulator is from about 0.03 mg/kg to 0.3 mg/kg.

15. The method of claim 1, wherein plant-derived proteoglycans are administered in combination with the plant-derived immunomodulator.

16. The method of claim 1, wherein the plant-derived immunomodulator comprises solanine.

17. The method of claim 1, wherein the plant-derived immunomodulator comprises chaconine.

18. The method of claim 1, wherein the plant-derived immunomodulator comprises solanine and chaconine.

* * * * *